(12) United States Patent
Lhermitte et al.

(10) Patent No.: US 7,777,045 B2
(45) Date of Patent: Aug. 17, 2010

(54) PROCESS FOR THE PREPARATION OF A 2-ETHYLAMINOPYRIDINE DERIVATIVE

(75) Inventors: Frédéric Lhermitte, Saint Symphorien d'ozon (FR); Gilles Perrin-Janet, Chaponnay (FR); Paul Dufour, Vaulx-en-Velin (FR); Pierre-Yves Coqueron, Lyons (FR)

(73) Assignee: Bayer Cropscience S.A. (FR)

( * ) Notice: Subject to any disclaimer, the term of this patent is extended or adjusted under 35 U.S.C. 154(b) by 134 days.

(21) Appl. No.: 11/793,501

(22) PCT Filed: Dec. 19, 2005

(86) PCT No.: PCT/EP2005/056900

§ 371 (c)(1),
(2), (4) Date: Sep. 17, 2007

(87) PCT Pub. No.: WO2006/067106

PCT Pub. Date: Jun. 29, 2006

(65) Prior Publication Data

US 2008/0114176 A1    May 15, 2008

(30) Foreign Application Priority Data

Dec. 21, 2004  (EP) .................... 04356202

(51) Int. Cl.
    *C07D 213/38*    (2006.01)
(52) U.S. Cl. .................... 546/329; 546/330; 546/337
(58) Field of Classification Search ................ 546/329, 546/330, 336, 337
    See application file for complete search history.

(56) References Cited

U.S. PATENT DOCUMENTS

| 5,208,247 | A | * | 5/1993 | Trova et al. | ................ 514/358 |
| 5,364,871 | A | * | 11/1994 | Takasugi et al. | ............ 514/342 |
| 6,215,024 | B1 | * | 4/2001 | Choudary et al. | .......... 564/138 |

FOREIGN PATENT DOCUMENTS

| EP | 1500651 | 1/2006 |
| WO | WO 2004/016088 | 2/2004 |
| WO | WO 2004/074280 | 9/2004 |

OTHER PUBLICATIONS

Mangus et al., J. Am. Chem. Soc., 1956, 78 (16), 4127-4130.*
Hsieh et al., Journal of Medicinal Chemistry, 1979, vol. 22, No. 10 1199-1206.*
Katsura et al., J. Med. Chem., 1994, 37 (1), 57-66.*

Chau-der Li et al.: Pyridine Derivatives as Potent Inducers of Erythroid Differentiation, J. Med. Chem., vol. 21, No. 9, 1978, pp. 874-877, XP002327632.
Kokars, V. et al., "Synthesis of 2-Azastilbene Derivatives with Intramolecular Charge Transfer," 38(7) Chemistry of Heterocyclic Compounds 805-809 (2002).
Magnus, G. et al., "The Pyridylethylation of Active Hydrogen Compounds," 78 J. Am. Chem. Soc. 4127-4129 (1956).
Katsura, Yousuke et al., "Studies on Antiulcer Drugs," 37(1) J. Med. Chem. 57-66 (1994).
Zakhs, E.R. et al., "Synthesis and Photochromic Properties of 2-(3-Nitro-2-pyridylmethyl) benzazoles," 71(7) Russian J. Gen. Chem. 1076-1087 (2001), ISSN 1070-3632.
Huang, C.Q. et al., "Design and synthesis of 3-(2-pyridyl)pyrazolo[1,5-a]pyrimidines as potent CRF1 receptor antagonists," 14 Bioorg. Med. Chem. Lett. 3943-3947 (2004).

* cited by examiner

*Primary Examiner* — Bernard Dentz
*Assistant Examiner* — David E Gallis
(74) *Attorney, Agent, or Firm* — Ostrolenk Faber LLP

(57) ABSTRACT

Process for the preparation of a 2-ethylaminopyridine derivative of general formula (I) or a salt thereof

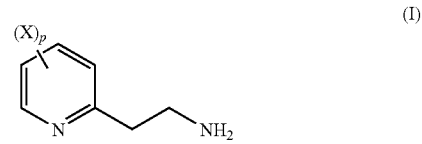

Process for the preparation of a N-[2-(2-pyridinyl)ethyl]carboxamide derivative of general formula (II) or a salt thereof

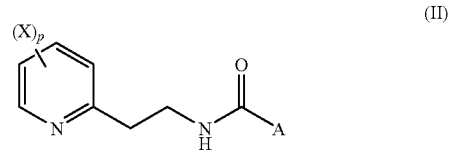

Intermediate of general formula (III)

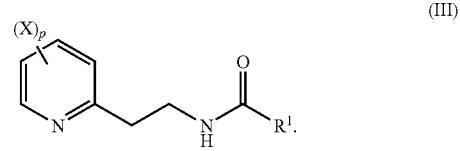

12 Claims, No Drawings

PROCESS FOR THE PREPARATION OF A 2-ETHYLAMINOPYRIDINE DERIVATIVE

CROSS REFERENCE TO RELATED APPLICATION(S)

The present application is a 35 U.S.C. § 371 national phase conversion of PCT/EP2005/056900 filed Dec. 19, 2005, which claims priority of European Application No. 04356202.4 filed Dec. 21, 2004.

The present invention relates to a novel process for the preparation of 2-ethylaminopyridine derivative which is useful as an intermediate compound for the preparation of pesticides, starting with 2-halogenopyridine derivative.

Patent application WO 2004/016088 discloses the preparation of N-[2-(2-pyridinyl)ethyl]benzamide derivatives starting from 2-halogenopyridine derivatives to produce 2-ethylaminopyridine derivatives and then coupling these 2-ethylaminopyridine derivatives with a halogenobenzoyl derivative. A step of this process consists in the reduction of a 2-methylcyanopyridine derivative into a 2-ethylaminopyridine in the presence of a metal catalyst in a protic solvent.

The process disclosed in this patent application presents the drawback in that the yield of the step of reduction of the 2-methylcyanopyridine derivative to produce a 2-ethylaminopyridine derivative is low and not acceptable at an industrial scale.

The process disclosed in this patent application also presents the drawback in that two separate steps are necessary for the preparation of the 2-methylcyanopyridine derivative starting from the 2-halogenopyridine derivative. This consequently increase the costs of the process and decrease its global yield, which is not acceptable at an industrial scale.

We have now found an alternative method to prepare 2-ethylaminopyridine derivative which overcomes these problems and which is applicable to industrial scale operation.

Accordingly, the present invention relates to a process for the preparation of a 2-ethylaminopyridine derivative of general formula (I) or a salt thereof

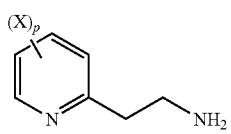

in which:
p is an integer equal to 1, 2, 3 or 4;
X is the same or different and is a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a (N—$C_1$-$C_8$-alkyl)oxycarbamoyl, a $C_1$-$C_8$-alkoxycarbamoyl, a (N—$C_1$-$C_8$-alkyl)-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkyl-sulphonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl or a phenylamino; and as to the N-oxides of 2-pyridine thereof; said process comprising:

(A)—a first step according to reaction scheme 1:

Scheme 1

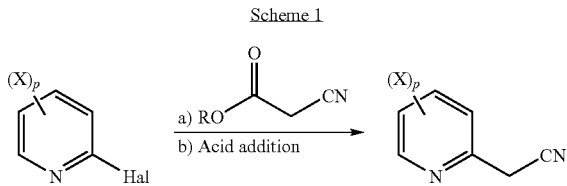

in which:
X and p are as defined above;
R is a $C_1$-$C_8$-alkyl; and
Hal represents a halogen atom;

comprising:
a) the reaction of a 2-halogenopyridine derivative with an alkyl cyanoacetate, in a 2-halogenopyridine derivative/alkyl cyanoacetate molar ratio of from 1 to 10, in a polar solvent, in the presence of a base, the base/2-halogenopyridine derivative molar ratio being of from 1 to 4;
b) followed by an addition of acid until a pH value of the reaction mixture of from 1 to 5;
to provide a 2-methylcyanopyridine derivative;

(B)—a second step according to reaction scheme 2:

Scheme 2

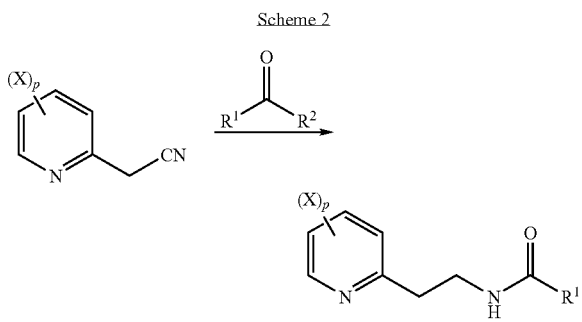

in which:

X, p are as defined above;

R¹ represents a $C_1$-$C_6$-alkyl;

R² represents a halogen atom or a —OCOAlk group; and Alk represents a $C_1$-$C_6$-alkyl;

comprising the catalytic reduction of reaction of a 2-methyl-cyanopyridine derivative obtained in step one in the presence of an acylating agent of formula R¹COR² and of a catalyst, in a solvent, under a hydrogen pressure of from 4 to 40 bar, to provide a 2-ethylaminopyridyl derivative;

(C)—a third step according to reaction scheme 3:

Scheme 3

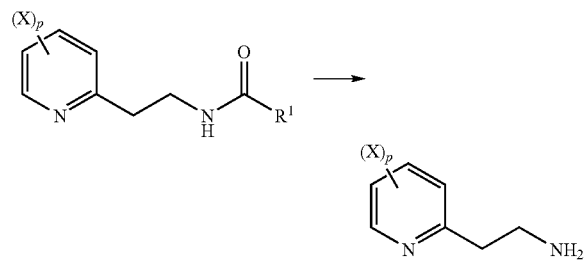

in which:

X and p are as defined above; and

R¹ represents a $C_1$-$C_6$-alkyl;

comprising the hydrolysis in water of a 2-ethylaminopyridine derivative obtained in step two by adding to it from 1 to 20 molar equivalent of an acid, at a temperature of from 20° C. to reflux, to provide a compound of general formula (I).

For the purposes of the present invention:

a halogen atom may be a bromine atom, a chlorine atom, a iodine atom or a fluorine atom. Preferably, halogen atom means chlorine atom;

carboxy means —C(=O)OH;

carbonyl means —C(=O)—;

carbamoyl means —C(=O)NH$_2$;

N-hydroxycarbamoyl means —C(=O)NHOH; and an alkyl group, an alkenyl group, and an alkynyl group as well as moieties containing these terms, can be linear or branched.

During the preparation of compound of general formula (I) according to the present invention, the preparation of the 2-methylcyanopyridine derivative starting from the 2-halogenopyridine derivative is made in only one step. Furthermore, the yield of the reduction step of a 2-methylcyanopyridine derivative into a 2-ethylaminopyridine derivative is of 65% to 95%. Such a process can thus be used at an industrial scale.

According to the present invention, the 2-pyridyl moiety may be substituted in any position by $(X)_p$, in which X and n are as defined above. Preferably, the present invention relates to the preparation of 2-ethylaminopyridine derivative of general formula (I) in which the different characteristics may be chosen alone or in combination as being:

as regards p, p is 1, 2 or 3. Preferably, p is 2.

as regards X, X is chosen, independently of the others, as being a halogen atom, a $C_1$-$C_8$-alkyl or a $C_1$-$C_8$-halogenoalkyl having 1 to 5 halogen atoms. More preferably, X is chosen, independently of the others, as being chlorine or CF$_3$;

as regards the positions in which the 2-pyridyl moiety is substituted by X, the 2-pyridyl moiety is substituted by X in 3- and/or in 5-position. Preferably, the 2-pyridyl moiety is substituted by X in 3- and 5-position The process of the present invention is particularly suitable for the preparation of:

N-2-[3-chloro-5-(trifluoromethyl)-2-pyridinyl]ethylamine, or

N-2-[3,5-dichloro-2-pyridinyl]ethylamine.

The first step (step A) of the process according to the present invention comprises the reaction of a 2-halogenopyridine derivative with an alkyl cyanoacetate, in a 2-halogenopyridine derivative/alkyl cyanoacetate molar ratio of from 1 to 10, in a polar solvent, in the presence of a base, the base/2-halogenopyridine derivative molar ratio being of from 1 to 4; followed by an addition of acid until a pH value of the reaction mixture of from 1 to 5 to provide a 2-methylcyanopyridine derivative. Preferably, step A may be conducted in the following conditions, chosen alone or in combination:

the polar solvent is chosen as being dimethylsulfoxide (DMSO), an ether solvent, an amide solvent or an urea solvent. More preferably, the solvent is chosen as being dimethylsulfoxide (DMSO), diethyl ether, diisopropyl ether, methyl tert-butyl-ether, methyl tert-amyl-ether, dioxane, tetrahydrofuran (THF), 1,2-di-methoxyethane, 1,2-di-ethoxy-ethane, anisole, N,N-dimethyl-formamide, N,N-dimethyl-acetamide, N-methyl-formanilide, N-methyl-pyrrolidone (NMP), hexamethyl-phosphoric-triamide or 1,3-dimethyl-2-2imidazolinone (DMA). Even more preferably, the solvent is chosen as being tetrahydrofuran (THIF), N-methyl-pyrrolidone (NMP), 1,3-dimethyl-2-2imidazolinone (DMA) or dimethylsulfoxide (DMSO);

the 2-halogenopyridine derivative/alkyl cyanoacetate molar ratio of from 1 to 5;

the alkyl cyanoacetate is chosen as being methylcyanoacetate, ethylcyanoacetate or terbutylcyanoacetate;

the base is chosen as being a alkaline earth metal base, a alkali metal hydride base, a hydroxide base, an amide base, an alcoholate base, an acetate base, a carbonate base, a hydrogen carbonate base or a tertiary amine base. More preferably, the base is chosen as being hydrogen carbonate base includes sodium hydride, sodium amide, lithium diisoproylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, ammonium carbonate, trimethylamine, triethylamine, tributyl-amine, N,N-dimethyl-aniline, N,N-di-methyl-benzylamine pyridine, N-methylpiperidine, N-methylmorpholine, N,N-dimethylaminopyridine, diazabicyclooctane (DABCO), diazabicyclononene (DBN) or diazabicycloundecene (DBU). Even more preferably, the base is chosen as being potassium hydroxide, sodium hydroxide, potassium bicarbonate, sodium bicarbonate or sodium hydride;

the base/2-halogenopyridine derivative molar ratio is of from 1 to 2.5;

the acid added is a mineral acid. Suitable mineral acid includes HCl and H$_2$SO$_4$. More preferably, HCl is added;

the acid is added until a pH value of the reaction mixture of from 2 to 4, more preferably of 2.

Step A does not necessarily require specific temperature conditions. Preferably, step A is conducted at a temperature of from 0° C. to reflux. More preferably, step A is conducted at a temperature of from 0° C. to 100° C.

The second step (step B) of the process according to the present invention comprises the catalytic reduction of reaction of a 2-methylcyanopyridine derivative obtained in step one in the presence of an acylating agent of formula $R^1COR^2$ and of a catalyst, in a solvent, under a hydrogen pressure of from 4 to 40 bar, to provide a 2-ethylaminopyridyl derivative. Preferably, step B may be conducted in the following conditions, chosen alone or in combination:

- the catalyst is a metallic catalyst Suitable metallic catalyst includes nickel-, platinum- or palladium-based catalyst such as Raney nickel, rhodium on alumina, palladium on charcoal, palladium on calcium carbonate, palladium on silica, palladium hydroxide, platinum on charcoal or platinum on alumina. More preferably, palladium on charcoal is used;
- the solvent is an organic acid. More preferably, the solvent is a $C_1$-$C_6$-alkanoic acid or formic acid. Suitable $C_1$-$C_6$-alkanoic acid includes acetic acid, propanoic acid, butanoic acid, pentanoic acid or hexanoic acid. Even more preferably, the solvent is acetic acid;
- the acylating agent is a $C_1$-$C_6$-alkanoic acid anhydride or formic anhydride. Suitable $C_1$-$C_6$-alkanoic acid anhydride includes acetic anhydride, propanoic anhydride, butanoic anhydride, pentanoic anhydride or hexanoic anhydride. Even more preferably, the acylating agent is acetic anhydride;
- the hydrogen pressure is of from 4 to 35 bars.

Step B does not necessarily require specific temperature conditions. Preferably, step B is conducted at a temperature of from 16° C. to 70° C. More preferably, step B is conducted at a temperature of from 20° C. to 40° C.

The third step (step C) of the process according to the present invention comprises the hydrolysis in water of a 2-ethylaminopyridine derivative obtained in step two by adding to it from 1 to 20 molar equivalent of an acid, at a temperature of from 20° C. to reflux, to provide a compound of general formula (I). Preferably, step C may be conducted in the following conditions, chosen alone or in combination:

- the added acid is a mineral acid. Suitable mineral acid includes HCl, $H_3PO_4$, $H_2SO_4$, HBr, HI or HF. More preferably, the acid is HCl or $H_2SO_4$. Even more preferably, the acid is HCl;
- 2 to 10 molar equivalents of acid are added the 2-ethylaminopyridinederivative obtained in step two (step B). More preferably, 5 molar equivalents of acid are added the 2-ethylaminopyridine derivative obtained in step two (step B);
- the reaction is conducted at reflux.

Compound of general formula (I) as defined above is a useful intermediate for the preparation of known pesticide compounds. These known pesticide compounds can be prepared by coupling a compound of general formula (I) as defined above with a halide benzoyl derivative. Thus, the present invention also relates to a process as defined above comprising a further step (D) according to the reaction scheme 4:

Scheme 4

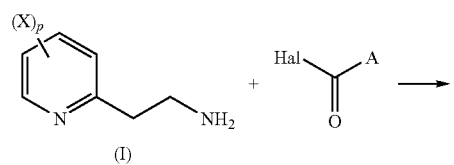

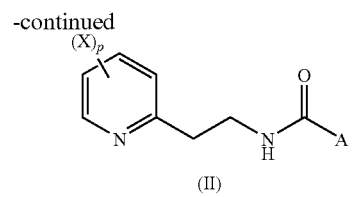

in which:

X and p are as defined above;

A represents a phenyl group or a 5-, 6- or 7-membered non-fused heterocycle with one, two or three heteroatoms which may be the same or different, the heterocycle being linked by a carbon atom; each of this group being optionally substituted by one or more substituents chosen independently of each other as being a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms or a $C_1$-$C_8$-alkylsulfonamide;

comprising the coupling reaction of the 2-ethylaminopyridine obtained in step three of the above described process with a halide carboxyl derivative contained in an organic solvent in the presence of a base to produce a N-[2-(2-pyridinyl)ethyl]carboxamide derivative of general formula (II).

According to the present invention, A may represent a five membered ring non-fused heterocycle. Specific examples of compounds prepared according to the process of the present invention where A is a five membered heterocycle include compound of general formula (II) wherein:

* A represents a heterocycle of the general formula (A-1)

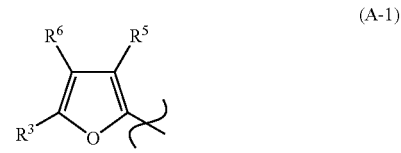

in which:

$R^3$ and $R^4$ may be the same or different and may be a hydrogen atom, a halogen atom, an amino group, a nitro group, a $C_1$-$C_4$-alkyl or a $C_1$-$C_4$-halogenoalkyl having 1 to 5 halogen atoms; and $R^5$ may be a halogen atom, a nitro group, a $C_1$-$C_4$-alkyl or a $C_1$-$C_4$-halogenoalkyl having 1 to 5 halogen atoms.

* A represents a heterocycle of the general formula (A-2)

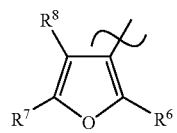

(A-2)

in which:
R⁶ may be a hydrogen atom, a halogen atom, a $C_1$-$C_4$-alkyl or a $C_1$-$C_4$-halogenoalkyl having 1 to 5 halogen atoms; and
R⁷ and R⁸ may be the same or different and may be a hydrogen atom, a halogen atom, an amino group, a $C_1$-$C_4$-alkyl or a $C_1$-$C_4$-halogenoalkyl having 1 to 5 halogen atoms.

* A represents a heterocycle of the general formula (A-3)

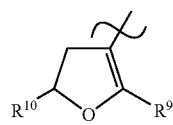

(A-3)

in which:
R⁹ may be a halogen atom, a $C_1$-$C_4$-alkyl or a $C_1$-$C_4$-halogenoalkyl having 1 to 5 halogen atoms; and
R¹⁰ may be a hydrogen atom, a $C_1$-$C_4$-alkyl or a $C_1$-$C_4$-halogenoalkyl having 1 to 5 halogen atoms.

* A represents a heterocycle of the general formula (A4)

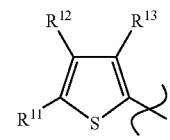

(A-4)

in which:
R¹¹ and R¹² may be the same or different and may be a hydrogen atom, a halogen atom, a $C_1$-$C_4$-alkyl, a $C_1$-$C_4$-halogenoalkyl having 1 to 5 halogen atoms, a $C_1$-$C_4$-alkylthio, a $C_1$-$C_4$-alkylsulphonyl, a phenyl optionally substituted by a halogen atom or a $C_1$-$C_4$-alkyl or a pyridyl optionally substituted by a halogen atom or a $C_1$-$C_4$-alkyl; and
R¹³ may be a halogen atom, a cyano group, a $C_1$-$C_4$-alkyl, a $C_1$-$C_4$-halogenoalkyl having 1 to 5 halogen atoms or a $C_1$-$C_4$-halogenoalkoxy having 1 to 5 halogen atoms.

* A represents a heterocycle of the general formula (A-5)

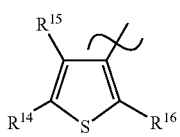

(A-5)

in which:
R¹⁴ and R⁵ may be the same or different and may be a hydrogen atom, a halogen atom, a $C_1$-$C_4$-alkyl, a $C_1$-$C_4$-alkyloxy or a $C_1$-$C_4$-halogenoalkyl having 1 to 5 halogen atoms; and
R¹⁶ may be a hydrogen atom, a halogen atom, a $C_1$-$C_4$-alkyl or a $C_1$-$C_4$-halogenoalkyl having 1 to 5 halogen atoms.

* A represents a heterocycle of the general formula (A-6)

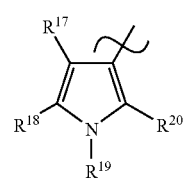

(A-6)

in which:
R¹⁷ may be a hydrogen atom, a halogen atom, a cyano group, a $C_1$-$C_4$-alkyl or a $C_1$-$C_4$-halogenoalkyl having 1 to 5 halogen atoms;
R¹⁸ and R²⁰ may be the same or different and may be a hydrogen atom, a halogen atom, a $C_1$-$C_4$-alkyl or a $C_1$-$C_4$-halogenoalkyl having 1 to 5 halogen atoms; and
R¹⁹ may be a hydrogen atom, a cyano group, a $C_1$-$C_4$-alkyl, a $C_1$-$C_4$-halogenoalkyl having 1 to 5 halogen atoms, a $C_1$-$C_4$-alkoxy-$C_1$-$C_4$-alkyl, a hydroxy-$C_1$-$C_4$-alkyl, a $C_1$-$C_4$-alkylsulphonyl, a di($C_1$-$C_4$-alkyl)aminosulphonyl, a $C_1$-$C_6$-alkylcarbonyl, a phenylsulphonyl optionally substituted by a halogen atom or a $C_1$-$C_4$-alkyl, or a benzoyl optionally substituted by a halogen atom or a $C_1$-$C_4$-alkyl.

* A represents a heterocycle of the general formula (A-7)

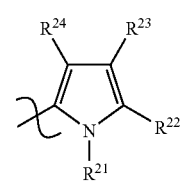

(A-7)

in which:
R²¹ may be a hydrogen atom, a cyano group, a $C_1$-$C_4$-alkyl, a $C_1$-$C_4$-halogenoalkyl having 1 to 5 halogen atoms, a $C_1$-$C_4$-alkoxy-$C_1$-$C_4$-alkyl, a hydroxy-$C_1$-$C_4$-alkyl, a $C_1$-$C_4$-alkylsulphonyl, a di($C_1$-$C_4$-alkyl)aminosulphonyl, a $C_1$-$C_6$-alkylcarbonyl, a phenylsulphonyl optionally substituted by a halogen atom or a $C_1$-$C_4$-alkyl, or a benzoyl optionally substituted by a halogen atom or a $C_1$-$C_4$-alkyl; and
R²², R²³ and R²⁴ may be the same or different and may be a hydrogen atom, a halogen atom, a cyano group, a $C_1$-$C_4$-alkyl, a $C_1$-$C_4$-halogenoalkyl having 1 to 5 halogen atoms or a $C_1$-$C_4$-alkylcarbonyl.

* A represents a heterocycle of the general formula (A-8)

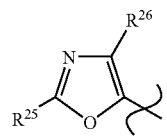
(A-8)

in which:
R$^{25}$ may be a hydrogen atom or a C$_1$-C$_4$-alkyl; and
R$^{26}$ may be a halogen atom, a C$_1$-C$_4$-alkyl or a C$_1$-C$_4$-halogenoalkyl having 1 to 5 halogen atoms.

* A represents a heterocycle of the general formula (A-9)

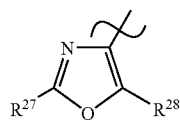
(A-9)

in which:
R$^{27}$ may be a hydrogen atom or a C$_1$-C$_4$-alkyl; and
R$^{28}$ may be a halogen atom, a C$_1$-C$_4$-alkyl, a C$_1$-C$_4$-halogenoalkyl having 1 to 5 halogen atoms or a phenyl optionally substituted by a halogen atom or a C$_1$-C$_4$-alkyl.

* A represents a heterocycle of the general formula (A-10)

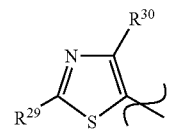
(A-10)

in which:
R$^{29}$ may be a hydrogen atom, a halogen atom, an amino group, a cyano group, a C$_1$-C$_4$-alkylamino, a di-(C$_1$-C$_4$-alkyl)amino, a C$_1$-C$_4$-alkyl, a C$_1$-C$_4$-halogenoalkyl having 1 to 5 halogen atoms or a phenyl optionally substituted by a halogen atom or a C$_1$-C$_4$-alkyl; and
R$^{30}$ may be a halogen atom, a C$_1$-C$_4$-alkyl or a C$_1$-C$_4$-halogenoalkyl having 1 to 5 halogen atoms.

* A represents a heterocycle of the general formula (A-11)

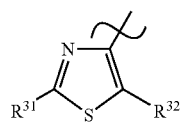
(A-11)

in which:
R$^{31}$ may be a hydrogen atom, a halogen atom, an amino group, a cyano group, a C$_1$-C$_4$-alkylamino, a di-(C$_1$-C$_4$-alkyl)amino, a C$_1$-C$_4$-alkyl or a C$_1$-C$_4$-halogenoalkyl having 1 to 5 halogen atoms; and
R$^{32}$ may be a halogen atom, a C$_1$-C$_4$-alkyl or a C$_1$-C$_4$-halogenoalkyl having 1 to 5 halogen atoms.

* A represents a heterocycle of the general formula (A-12)

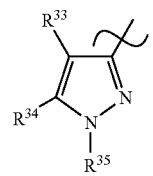
(A-12)

in which:
R$^{33}$ may be a halogen atom, a cyano group, a nitro group, a C$_1$-C$_4$-alkyl, a C$_1$-C$_4$-halogenoalkyl having 1 to 5 halogen atoms, a C$_3$-C$_6$-cycloalkyl, a C$_1$-C$_4$-alkoxy, a C$_1$-C$_4$-halogenoalkoxy having 1 to 5 halogen atoms, a C$_1$-C$_4$-alkylthio, a C$_1$-C$_4$-halogenoalkylthio having 1 to 5 halogen atoms, an aminocarbonyl group or an aminocarbonyl-C$_1$-C$_4$-alkyl;
R$^{34}$ may be a hydrogen atom, a halogen atom, a cyano group, a nitro group, a C$_1$-C$_4$-alkyl, a C$_1$-C$_4$-alkoxy or a C$_1$-C$_4$-alkylthio; and
R$^{35}$ may be a hydrogen atom, a phenyl, a C$_1$-C$_4$-alkyl, a C$_1$-C$_4$-halogenoalkyl having 1 to 5 halogen atoms, a hydroxy-C$_1$-C$_4$-alkyl, a C$_2$-C$_6$-alkenyl, a C$_3$-C$_6$-cycloalkyl, a C$_1$-C$_4$-alkylthio-C$_1$-C$_4$-alkyl, a C$_1$-C$_4$-halogenoalkylthio-C$_1$-C$_4$-alkyl having 1 to 5 halogen atoms, a C$_1$-C$_4$-alkoxy-C$_1$-C$_4$-alkyl or a C$_1$-C$_4$-halogenoalkoxy-C$_1$-C$_4$-alkyl having 1 to 5 halogen atoms.

* A represents a heterocycle of the general formula (A-13)

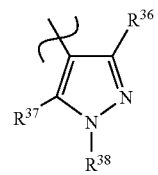
(A-13)

in which:
R$^{36}$ may be a hydrogen atom, a halogen atom, a cyano group, a nitro group, a C$_1$-C$_4$-alkyl, a C$_1$-C$_4$-halogenoalkyl having 1 to 5 halogen atoms, a C$_3$-C$_6$-cycloalkyl, a C$_1$-C$_4$-alkoxy, a C$_1$-C$_4$-halogenoalkoxy having 1 to 5 halogen atoms, a C$_1$-C$_4$-alkylthio, a C$_1$-C$_4$-halogenoalkylthio having 1 to 5 halogen atoms, an aminocarbonyl or an aminocarbonyl-C$_1$-C$_4$-alkyl;
R$^{37}$ may be a hydrogen atom, a halogen atom, a cyano group, a C$_1$-C$_4$-alkyl, a C$_1$-C$_4$-alkoxy, a C$_1$-C$_4$-halogenoalkoxy having 1 to 5 halogen atoms or a C$_1$-C$_4$-alkylthio; and
R$^{38}$ may be a hydrogen atom, a C$_1$-C$_4$-alkyl, a C$_1$-C$_4$-halogenoalkyl having 1 to 5 halogen atoms, a hydroxy-C$_1$-C$_4$-alkyl, a C$_2$-C$_6$-alkenyl, a C$_3$-C$_6$-cycloalkyl, a C$_1$-C$_4$-alkylthio-C$_1$-C$_4$-alkyl, a C$_1$-C$_4$-halogenoalkylthio-C$_1$-C$_4$-alkyl having 1 to 5 halogen atoms, a C$_1$-C$_4$-alkoxy-C$_1$-C$_4$-alkyl, a C$_1$-C$_4$-halogenoalkoxy-C$_1$-C$_4$-alkyl having 1 to 5 halogen atoms or a phenyl optionally substituted by a halogen atom, a C$_1$-C$_4$-alkyl, a C$_1$-C$_4$-alkoxyalkyl or a nitro group.

* A represents a heterocycle of the general formula (A-14)

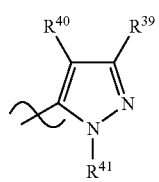
(A-14)

in which:

$R^{39}$ may be a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl, or an aminocarbonyl-$C_1$-$C_4$-alkyl;

$R^{40}$ may be a hydrogen atom, a halogen atom, a cyano group, a $C_1$-$C_4$-alkyl, a $C_1$-$C_4$-alkoxy, a $C_1$-$C_4$-alkylthio or a $C_1$-$C_4$-halogenoalkyl having 1 to 5 halogen atoms;

$R^{41}$ may be a hydrogen atom, a phenyl, a benzyl, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl, a $C_1$-$C_4$-halogenoalkoxy-$C_1$-$C_4$-alkyl having 1 to 5 halogen atoms.

* A represents a heterocycle of the general formula (A-15)

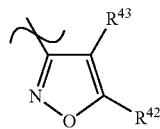
(A-15)

in which:

$R^{42}$ may be a hydrogen atom, a halogen atom, a $C_1$-$C_4$-alkyl or a $C_1$-$C_4$-halogenoalkyl having 1 to 5 halogen atoms; and $R^{43}$ may be a halogen atom, a $C_1$-$C_4$-alkyl or a $C_1$-$C_4$-halogenoalkyl having 1 to 5 halogen atoms.

* A represents a heterocycle of the general formula (A-16)

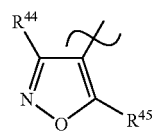
(A-16)

in which $R^{44}$ and $R^{45}$ may be the same or different and may be a hydrogen atom, a halogen atom, a $C_1$-$C_4$-alkyl, a $C_1$-$C_4$-halogenoalkyl having 1 to 5 halogen atoms, a phenyl optionally substituted by a halogen atom or a $C_1$-$C_4$-alkyl, or a heterocyclyl optionally substituted by a halogen atom or a $C_1$-$C_4$-alkyl.

* A represents a heterocycle of the general formula (A-17)

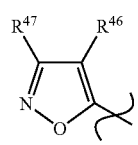
(A-17)

in which $R^{46}$ may be a halogen atom, a $C_1$-$C_4$-alkyl or a $C_1$-$C_4$-halogenoalkyl having 1 to 5 halogen atoms. and $R^{47}$ may be a halogen atom, a $C_1$-$C_4$-alkyl or a $C_1$-$C_4$-halogenoalkyl having 1 to 5 halogen atoms.

* A represents a heterocycle of the general formula (A-18)

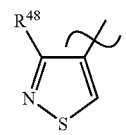
(A-18)

in which $R^{48}$ may be a halogen atom, a $C_1$-$C_4$-alkyl or a $C_1$-$C_4$-halogenoalkyl having 1 to 5 halogen atoms.

* A represents a heterocycle of the general formula (A-19)

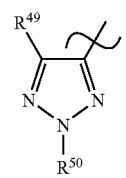
(A-19)

in which:

$R^{49}$ may be a halogen atom, a $C_1$-$C_4$-alkyl or a $C_1$-$C_4$-halogenoalkyl having 1 to 5 halogen atoms; and $R^{50}$ may be a hydrogen atom, a $C_1$-$C_4$-alkyl, a $C_1$-$C_4$-halogenoalkyl having 1 to 5 halogen atoms, or a phenyl optionally substituted by a halogen atom or a $C_1$-$C_4$-alkyl.

* A represents a heterocycle of the general formula (A-20)

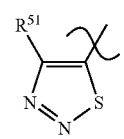
(A-20)

in which $R^{51}$ may be a halogen atom, a $C_1$-$C_4$-alkyl or a $C_1$-$C_4$-halogenoalkyl having 1 to 5 halogen atoms.

According to the present invention, A may also represent a six membered ring non-fused heterocycle. Specific examples of compounds prepared according to the process of the present invention where A is a six membered heterocycle include:

* A represents a heterocycle of the general formula (A-21)

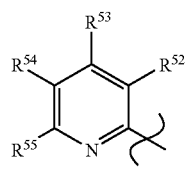

in which:
- $R^{52}$ may be a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms or a $C_1$-$C_4$-halogenoalkoxy having 1 to 5 halogen atoms;
- $R^{53}$, $R^5$ and $R^{55}$, which may be the same or different, may be a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl or a $C_1$-$C_4$-alkylsulphonyl.

* A represents a heterocycle of the general formula (A-22)

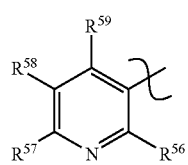

in which:
- $R^{56}$ may be a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_5$-alkylthio, a $C_2$-$C_5$-alkenylthio a $C_1$-$C_4$-halogenoalkylthio having 1 to 5 halogen atoms, a $C_1$-$C_4$-halogenoalkoxy having 1 to 5 halogen atoms, a phenyloxy optionally substituted by a halogen atom or a $C_1$-$C_4$-alkyl, or a phenylthio optionally substituted by a halogen atom or a $C_1$-$C_4$-alkyl;
- $R^{57}$, $R^{58}$ and $R^{59}$, which may the same or different, may be a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl, a $C_1$-$C_4$-alkylsulphonyl or a N-morpholine optionally substituted by a halogen atom or a $C_1$-$C_4$-alkyl, or a thienyl optionally substituted by a halogen atom or a $C_1$-$C_4$-alkyl.

* A represents a heterocycle of the general formula (A-23)

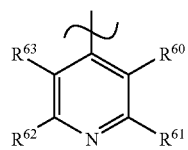

in which $R^{60}$, $R^{61}$, $R^{62}$ and $R^{63}$, which may be the same or different, may be a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms, a $C_1$-$C_4$-halogenoalkoxy having 1 to 5 halogen atoms, a $C_1$-$C_4$-alkylsulphinyl or a $C_1$-$C_4$-alkylsulphonyl.

* A represents a heterocycle of the general formula (A-24)

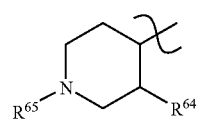

in which:
- $R^{64}$ may be a halogen atom, a $C_1$-$C_4$-alkyl or a $C_1$-$C_4$-halogenoalkyl having 1 to 5 halogen atoms;
- $R^{65}$ may be a hydrogen atom, a $C_1$-$C_4$-alkyl, a $C_1$-$C_4$-halogenoalkyl having 1 to 5 halogen atoms, a $C_1$-$C_6$-alkoxycarbonyl, a benzyl optionally substituted by 1 to 3 halogen atoms, a benzyloxycarbonyl optionally substituted by 1 to 3 halogen atoms or a heterocyclyl.

* A represents a heterocycle of the general formula (A-25)

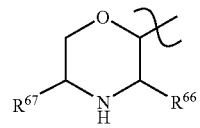

in which:
- $R^{66}$ may be a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms or a $C_1$-$C_4$-halogenoalkoxy having 1 to 5 halogen atoms;
- $R^{67}$ may be a hydrogen atom, a $C_1$-$C_4$-alkyl, a $C_1$-$C_4$-halogenoalkyl having 1 to 5 halogen atoms or a benzyl.

* A represents a heterocycle of the general formula (A-26)

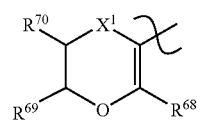

in which:
- $X^1$ may be a sulphur atom, —SO—, —SO$_2$— or —CH$_2$—;
- $R^{68}$ may be a $C_1$-$C_4$-alkyl or a $C_1$-$C_4$-halogenoalkyl having 1 to 5 halogen atoms; and
- $R^{69}$ and $R^{70}$ may be the same or different and may be a hydrogen atom or a $C_1$-$C_4$-alkyl.

* A represents a heterocycle of the general formula (A-27)

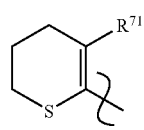

in which:
R$^{71}$ may be a C$_1$-C$_4$-alkyl or a C$_1$-C$_4$-halogenoalkyl having 1 to 5 halogen atoms;

* A represents a heterocycle of the general formula (A-28)

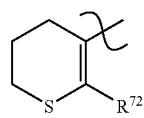

in which:
R$^{72}$ may be a C$_1$-C$_4$-alkyl or a C$_1$-C$_4$-halogenoalkyl having 1 to 5 halogen atoms.

* A represents a heterocycle of the general formula (A-29)

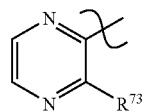

in which R$^{73}$ may be a halogen atom, a C$_1$-C$_4$-alkyl or a C$_1$-C$_4$-halogenoalkyl having 1 to 5 halogen atoms.

According to the present invention, A may also represent an optionally substituted phenyl group. Preferably, the present invention relates to the preparation of N-[2-(2-pyridinyl)ethyl]carboxamide derivative of general formula (II) in which A is a phenyl group and in which the different characteristics may be chosen alone or in combination as being:

A is substituted by 1 or 2 substituents. More preferably, A is substituted by 1 substituent.

each substituent is chosen, independently of the others, as being a hydrogen atom, a halogen atom, a C$_1$-C$_8$-alkyl or a C$_1$-C$_8$-halogenoalkyl having 1 to 5 halogen atoms. More preferably each substituent is chosen, independently of the others, as being chlorine or CF$_3$;

the phenyl moiety is substituted in ortho position.

Such a process is particularly suitable for the preparation of a compound of formula (II) which is:
N-{2-[3-chloro-5-(trifluoromethyl)-2-pyridinyl]ethyl}-2-trifluoromethylbenzamide;
N-{2-[3-chloro-5-(trifluoromethyl)-2-pyridinyl]ethyl}-2-iodobenzamide; or
N-{2-[3,5-dichloro-2-pyridinyl]ethyl}-2-trifluoromethylbenzamide.

The fourth step (step D) of the process according to the present invention comprises the coupling reaction the 2-ethylaminopyridine obtained in step C with a halide benzoyl derivative to provide a compound of general formula (II) as defined above. Such a coupling reaction may be performed by known methods. Such a coupling reaction may for example be conducted according to the Schotten-Baumann reaction described in Schotten Ber. 1884, 17, 2544 and Baumann Ber. 1886, 19, 3218, herein incorporated by reference.

The compounds of general formula (I) and of formula (II) according to the present invention can be prepared according to the above described process. It will nevertheless be understood that, on the basis of his general knowledge and of available publications, the skilled worker will be able to adapt this method according to the specifics of each of the compounds, which it is desired to synthesise.

Certain of the intermediates used for the preparation of compound of general formula (I) are novel. Therefore, the present invention also relates to novel intermediate compounds useful for the preparation of compound of general formula (I). Thus, according to the present invention, there is provided a compound of general formula (III)

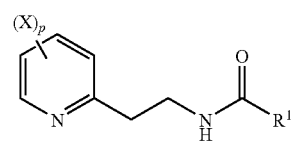

in which:
X and p are as defined above; and
R$^1$ represents a C$_1$-C$_6$-alkyl group.

The present invention will now be illustrated with reference to the following examples.

Preparation, of 3-chloro-5-(trifluoromethyl)-2-ethylamine-pyridinyl

Step 1: Preparation of a 3-chloro-5-(trifluoromethyl)-2-methylcyanopyridine

A two-necked round bottom flask equipped with a magnetic bar, a thermometer and a reflux condenser was charged with the 2,3-dichloro-5-(trifluoromethyl)-pyridine in NMP (14.6% w/v), KOH (2.2 equiv.). The solution was heated to 70° C. and the ethyl cyanoacetate (1.2 equiv.) was added slowly. After the addition the reaction medium was heated 3 h. HCl aq. 36% was added to obtained pH 2 and the mixture was heated to 130° C. for 2 h. At 20° C., NaOH aq. 1N was added and the aqueous phase was extracted 3 times with methyl tertbutyl ether (MTBE). The organic phases were combined, washed with water, dried over MgSO$_4$ and concentrated to the dryness. The isolated yield was 94%.

NMR$^1$H (300 Mz, CDCl$_3$): 4.15 (s, 2H, C$\underline{H}_2$), 8.0 (s, 1H, Hpyr.), 8.79 (s, 1H, Hpyr.).

Step 2: Preparation of a 3-chloro-5-(trifluoromethyl)-2-ethylacetamide-pyridinyl A hydrogenation reactor was charged with 3-chloro-5-trifluoromethyl-2-methylcyano pyridine (7 g, 31.4 mMol), Pd/C$_5$% (1.05 g), Ac$_2$O (12.8 g, 125.8 mMol, 4 equiv.), AcOH (60 ml). The reactor was stirred under 30 bars of hydrogen at 20° C. for 5 hours. The hydrogen was removed, the catalyst filtrated out and the solvent was evaporated. 8.4 g of crude desired product was obtained. HPLC titrated yield=71%.

Mass spectrum: 266 DA, MH$^+$: 267

Step 3: Preparation of a 3-chloro-5-(trifluoromethyl)-2-ethylamine-pyridinyl A two-necked round bottom flask equipped with a magnetic bar, a thermometer and a reflux condenser was charged with the above crude 3-chloro-5-(trifluoromethyl)-2-ethylacetamide-pyridinyl (22.2 mMol), water (50 ml), HCl 37% (4.3 g, 5 equiv.). The solution was refluxed 5 hours. The aqueous phase was washed 3 times with $CH_2Cl_2$ (3×20 ml) at room temperature. The aqueous phase was titrated by HPLC. The titrated yield in solution is 92%.

Mass spectrum analysis: 224 DA, $MH^+$225.

Under these conditions, the global yield to prepare the 2-ethylaminopyridyl derivative starting from 2-methylcyanopyridine derivative (step 2 and step 3) is 65%, which is acceptable at an industrial scale.

Comparative experiments by using the process disclosed in patent application WO 2004/016088 have been conducted:

Preparation of a 3-chloro-5-trifluoromethyl)-2-ethylamine-pyridinyl starting from 3-chloro-5-(trifluoromethyl)-2-methylcyanopyridine according to the process disclosed in WO 2004/016088

A hydrogenation reactor was charged with 3-chloro-5-trifluoromethyl-2-methylcyano pyridine (1.5 g, 6.72 mMol), $Pd/C_5$%, AcOH (7 ml). The reactor was stirred under 6 bars of hydrogen at 20° C. for 15 hours. The hydrogen was removed, the catalyst filtrated out and the solvent was evaporated. 1.4 g of crude desired product was obtained. Titrated yield by HPLC is 19%.

Mass spectrum analysis: 224 DA, $MH^+$225.

Under these conditions, the global yield to prepare the 2-ethylaminopyridyl derivative starting from 2-methylcyanopyridine derivative is only 19%, which is not acceptable at an industrial scale.

Above described step 3 may be completed by a further step for preparing N-{2-[3-chloro-5-(trifluoromethyl)-2-pyridinyl]ethyl}-2-trifluoromethylbenzamide which is known as fungicide:

Step 4: Preparation of a N-{2-[3-chloro-5-(trifluoromethyl)-2-pyridinyl]ethyl}-2-trifluoromethylbenzamide A two-necked round bottom flask equipped with a magnetic bar, a thermometer and a reflux condenser was charged with the above aqueous solution, the 2-trifluoromethyl benzoic acid chloride (1.2 eq.) solution in THF (80 ml) was added followed by NaOH aqueous 2N until pH is 8. After 1 hour, the aqueous phase was extracted with $iPr_2O$ (40 ml), the organic phases were mixed, washed with HCl aqueous 1N (2×40 ml) and water (40 ml). The organic phase was titrated by HPLC. The titrated yield in solution was 90%.

Heptane (70 ml) was added to the organic solution and the THF and $iPr_2O$ were distilled to obtain precipitation of the desired compound. After filtration, the cake was washed with heptane/$CH_2Cl_2$ (90/10) and dried. The isolated yield was 80%.

The invention claimed is:

1. A process for the preparation of a 2-ethylaminopyridine derivative of general formula (I) or a salt thereof

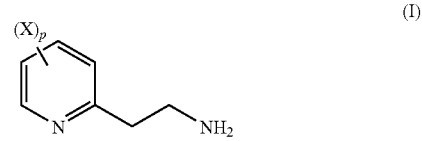

in which:

p is an integer equal to 1, 2, 3 or 4;

X is independently selected from the group consisting of a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a (N—$C_1$-$C_8$-alkyl)oxycarbamoyl, a $C_1$-$C_8$-alkoxycarbamoyl, a (N—$C_1$-$C_8$-alkyl)-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a ($C_1$-$C_6$-alkoxyimino)-$C_1$-$C_6$-alkyl, a (C1-C6-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl and a phenylamino; and as to the N-oxides of 2-pyridine thereof;

said process comprising:

(A) a first step according to reaction scheme 1

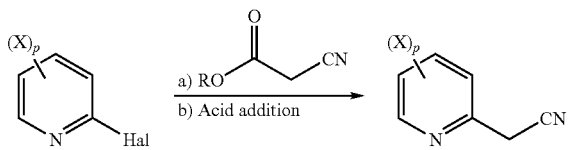

in which:

X and p are as defined above;

R is a $C_1$-$C_8$-alkyl; and

Hal represents a halogen atom;
comprising:
 a) the reaction of a 2-halogenopyridine derivative with an alkyl cyanoacetate, in a 2-halogenopyridine derivative/alkyl cyanoacetate molar ratio of from 1 to 10, in a polar solvent, in the presence of a base, the base/2-halogenopyridine derivative molar ratio being of from 1 to 4;
 b) followed by an addition of acid until a pH value of the reaction mixture of from 1 to 5;
to provide a 2-methylcyanopyridine derivative;
wherein said first step (A) is conducted at a temperature of from 0° C. to reflux;
 (B) a second step according to reaction scheme 2:

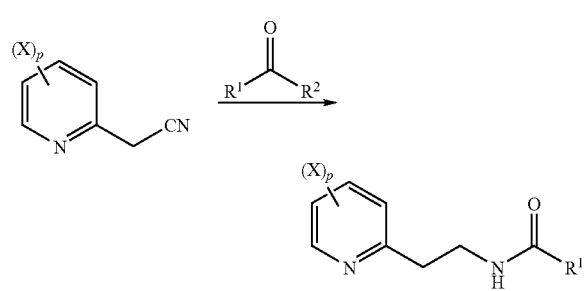

Scheme 2 in which:
 X and p are as defined above;
 $R^1$ represents a $C_1$-$C_6$-alkyl;
 R2 represents a halogen atom or a —OCOAlk group; and Alk represents a $C_1$-$C_6$-alkyl;
comprising the catalytic reduction of reaction of a 2-methylcyanopyridine derivative obtained in the first step in the presence of an acylating agent of formula $R^1COR^2$ and of a catalyst, in a solvent, under a hydrogen pressure of from 4 to 40 bar, to provide a 2-ethylaminopyridyl derivative;
 (C) a third step according to reaction scheme 3:

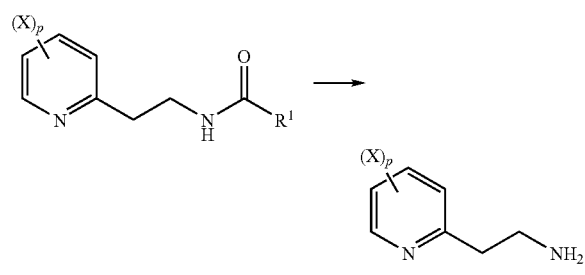

Scheme 3 in which:
 X and p are as defined above; and
 $R^1$ represents a $C_1$-$C_6$-alkyl group;
comprising the hydrolysis in water of a 2-ethylaminopyridine derivative obtained in the second step by adding to it from 1 to 20 molar equivalent of an acid, at a temperature of from 20° C. to reflux, to provide a compound of general formula (I).

2. The process claim 1 wherein p is 2.

3. The process of claim 1 wherein each X is independently selected from the group consisting of chlorine and $CF_3$.

4. The process claim 1 wherein the 2-pyridyl moiety is substituted by X in the 3-and/or in the 5-position.

5. The process of claim 1 wherein the compound of formula (I) is selected from the group consisting of:
 N-2[3-chloro-5-(trifluoromethyl)-2-pyridinyl]ethylamine, and
 N-2-[3,5-dichloro-2-pyridinyl]ethylamine.

6. The process of claim 1, wherein the second step (B) is conducted at a temperature of from 16° C. to 70° C.

7. The process claim 1 further comprising a step (D) according to the reaction scheme 4:

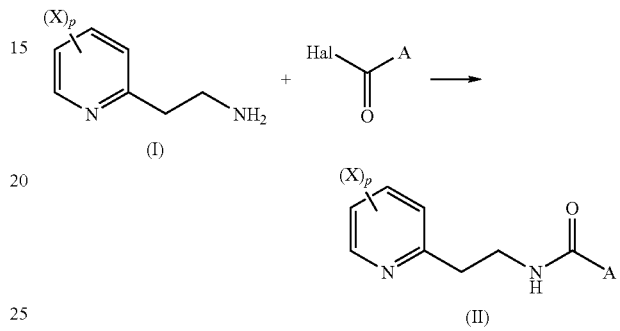

Scheme 4 in which:
 X and p are as defined above;
 A is selected from the group consisting of a phenyl group and a 5-, 6-or 7-membered non-fused heterocycle having one, two or three heteroatoms which may be the same or different, the heterocycle being linked by a carbon atom; each of this group being optionally substituted by one or more substituents independently selected from the group consisting of a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms and a $C_1$-$C_8$-alkylsulfonamide;
comprising the coupling reaction of the 2-ethylaminopyridine obtained in the third step of said process of claim 1 with a halide carboxyl derivative contained in an organic solvent in the presence of a base to produce a N-[2-(2-pyridinylethyl] carboxamide derivative of general formula (II).

8. The process claim 7 wherein A is a phenyl group.

9. The process of claim 8 wherein A is substituted by one or two substituents.

10. The process of claim 8 wherein each substituent of A is independently selected from the group consisting of chlorine and $CF_3$.

11. The process of claim 8 wherein the A is substituted in an ortho position.

12. The process of claim 7 wherein compound of formula (II) is selected from the group consisting of:
   N-{2[3-chloro-5-trifluoromethyl)-2-pyridinyl]ethyl}-2-trifluoromethylbenzamide;
   N-{2[3-chloro-5-trifluoromethyl)-2-pyridinyl]ethyl}-2-iodobenzamide; and
   N-{2-[3,5-dichloro-2-pyridinyl]ethyl}-2-trifluoromethyl-benzamide.

* * * * *